United States Patent [19]
Lim et al.

[11] Patent Number: 5,961,666
[45] Date of Patent: Oct. 5, 1999

[54] HAIR DYE COMPOSITIONS CONTAINING 3-SUBSTITUTED-4-AMINOPHENOLS AND 2-SUBSTITUTED-1-NAPHTHOLS

[76] Inventors: Mu-Ill Lim, 31 Mayflower Dr., Trumbull, Conn. 06611; Yuh-Guo Pan, 119 Woodridge Dr., Stamford, Conn. 06905; James S. Anderson, 1 Summit La., Bethel, Conn. 06801

[21] Appl. No.: 08/974,217

[22] Filed: Nov. 19, 1997

[51] Int. Cl.⁶ .................................................. A61K 7/13
[52] U.S. Cl. ........................................ 8/408; 8/421; 8/424
[58] Field of Search ............................... 8/406, 408, 421, 8/424

[56] References Cited

U.S. PATENT DOCUMENTS

| | | | |
|---|---|---|---|
| 3,210,252 | 10/1965 | Blanke et al. | 8/408 |
| 4,169,703 | 10/1979 | Fahouri | 8/421 |
| 4,883,656 | 11/1989 | Konrad et al. | 8/408 |
| 5,344,463 | 9/1994 | Chan et al. | 8/408 |
| 5,409,503 | 4/1995 | Clausen et al. | 8/408 |
| 5,500,021 | 3/1996 | Cotteret et al. | 8/408 |
| 5,514,188 | 5/1996 | Cotteret et al. | 8/408 |
| 5,567,421 | 10/1996 | Cotteret et al. | 8/408 |
| 5,580,357 | 12/1996 | Cotteret et al. | 8/421 |

*Primary Examiner*—Caroline D. Liott
*Attorney, Agent, or Firm*—Morton S. Simon

[57] ABSTRACT

A 2-Substituted-1-naphthol of the formula:

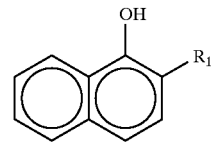

wherein $R_1$ is $C_1$–$C_6$ alkyl or monohydroxy $C_1$–$C_6$ alkyl couples with a primary intermediate of the formula:

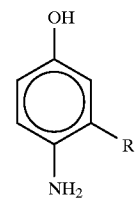

wherein R is $C_1$–$C_6$ alkyl or monohydroxy $C_1$–$C_6$ alkyl to produce an oxidative dye.

11 Claims, No Drawings

HAIR DYE COMPOSITIONS CONTAINING 3-SUBSTITUTED-4-AMINOPHENOLS AND 2-SUBSTITUTED-1-NAPHTHOLS

FIELD OF INVENTION

The present invention relates to oxidative keratinous dyeing compositions based on 4-aminophenols and 1-naphthols.

BACKGROUND OF THE INVENTION

U.S. Pat. No. 3,210,252 discloses oxidation dyeing compositions containing 5-amino-2-methylphenol (1-methyl-2-hydroxy-4-aminobenzene) in combination with p-phenylene-diamine (PPD) or PPD derivatives or p-aminophenol (PAP) or PAP derivatives. In the presence of an oxidizing agent these compositions dye hair brilliant color shades such as gold red, mahogany and Bordeaux. PAP derivatives include compounds such as 3-methyl-4-aminophenol and 2-methyl-4-aminophenol.

U.S. Pat. No. 4,883,656 (the '656 patent) covers compositions for the oxidative dyeing of hair comprising a specific composition of 3-methyl-4-aminophenol, 2-methyl-5-aminophenol and PPD or p-toluenediamine (PTD) or mixtures thereof. Natural red, free of yellow and blue hues, was obtained.

The '656 patent teaches that 3-methyl-4-aminophenol is not good in conventional terms. It is disclosed that "although the developer substance 3-methyl-4-aminophenol is frequently mentioned in publications on hair dyeing, it has achieved very little importance, if any, in practice. Thus, 3-methyl-4-aminophenol with 2-methyl-5-aminophenol as coupler only provides a brick red which is weak in color."

U.S. Pat. No. 4,997,451 ('451 patent) relates to oxidative hair dyeing compositions based on 4-aminophenol derivatives and new 4-aminophenol derivatives.

The '451 patent covers dyeing compositions containing 2-(alkoxymethyl)-4-aminophenol as the developer substance and teaches that "the 4-amino-3-methylphenol, which is a structurally similar compound, results in a considerably reduced color depth than the 4-aminophenol derivatives of the present invention."

U.S. Pat. No. 5,344,463 (the '463 patent) relates to hair dye compositions and methods utilizing 2-substituted-1-naphthol couplers.

The '463 patent deals with dye composition containing 2-substituted-1-naphthol in which the composition imparts a long-lasting red color to hair. The compositions of this patent are taught to be substantially more acid-resistant than dyestuffs prepared through use of the 1-naphthol coupler.

3-Methyl-4-aminophenol is mentioned as one of the primary intermediates in the '463 patent. However, there is no teaching that the combination of 3-methyl-4-aminophenol and 2-methyl-1-naphthol delivers color to hair which is unusually and unexpectedly shampoo- and light-fast.

U.S. Pat. No. 5,500,021 ('021 patent) relates to an oxidation dye composition for keratinous fibers comprising a para-aminophenol, a meta-aminophenol and a meta-phenylenediamine, and dyeing process using such a composition.

The combination of 3-methyl-4-aminophenol, 2-methyl-5-aminophenol and PPD or PTD produces coloration with warm and coppery shades which have good resistance to light, to washing, to bad weather, and to perspiration. The '021 patent teaches that the composition gives resistance to perspiration which is particularly noteworthy and superior to that of the state of the art.

U.S. Pat. No. 5,514,188 discloses oxidation dye compositions for keratinous fibers comprising a 4-aminophenol, 2-methyl-5-aminophenol and p-phenylenediamine and/or a bis(phenylalkylene)diamine.

Combinations of 3-Methyl-4-aminophenol or 2-methyl-4-aminophenol, or 2-hydroxymethyl-4-aminophenol with 2-methyl-5-aminophenol and PPD derivatives produce colorations with red or coppery shades which are resistant to light, to washing, to bad weather, and to perspiration.

U.S. Pat. No. 4,883,656 characterizes 3-methyl-4-aminophenol as achieving very little importance in practice and that compositions containing this intermediate provide a brick red which is weak in color.

U.S. Pat. No. 4,997,451 also teaches that 3-methyl-4-aminophenol produces a considerably reduced color depth than 4-aminophenol.

U.S. Pat. Nos. 4,883,656 and 4,997,451 teach that 3-methyl-4-aminophenol does not produce good color useful enough to use as a hair dye. U.S. Pat. No. 5,500,021 and U.S. Pat. No. 5,514,188 also teach that 3-methyl-4-aminophenol is only useful when it is used in combination with 2-methyl-5-aminophenol and m-diaminobenzene or p-diaminobenzene.

SUMMARY OF THE INVENTION

The present invention relates to a dyeing composition for keratinous fibers, and in particular, for human keratinous fibers, said composition comprising 3-alkyl-4-aminophenol and 2-alkyl-1-naphthol and to a dyeing process using this combination.

DETAILED DESCRIPTION OF THE INVENTION

It has surprisingly been found that the use of the combination of a 3-alkyl-4-aminophenol and 2-alkyl-1-naphthol has several advantages.

U.S. Pat. Nos. 4,883,656 and 4,997,451 teach that when used with only one coupler 3-methyl-4-aminophenol is expected to deliver weaker coloration to hair than 4-aminophenol. To the present inventors' surprise, the color depth obtained from 3-methyl-4-aminophenol (3-Mepap) and 2-methyl-1-naphthol is as strong as 4-aminophenol on gray hair and significantly stronger on bleached hair.

Wash fastness of the dye produced by coupling 3-methyl-4-aminophenol with 2-methyl-1-naphthol, is far better than the wash fastness of the dye produced by coupling 4-aminophenol with 2-methyl-1-naphthol. The ΔE value of the dye resulting from the former intermediate is smaller than the value of the dye resulting from latter intermediate (see Table 3, below). ΔE indicates the magnitude of the color difference. The smaller the ΔE value, the better the fastness. ΔE is defined as $$\sqrt{(\Delta L)^2 + (\Delta a)^2 + (\Delta b)^2}$$

wherein L is a measure of color depth (i.e. darkness) a and b indicate color directions: +a is the red direction; −a is the green direction; +b is the yellow direction; and −b is the blue direction.

The present invention relates to the use of 2-substituted-1-naphthols of the general formula I:

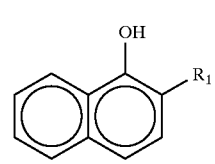

(I)

wherein $R_1$ is $C_1$–$C_6$ alkyl or monohydroxy $C_1$–$C_6$ alkyl.

Preferred couplers in this aspect of the invention are:

2-methyl-1-naphthol, 2-hydroxymethyl-1-naphthol;
2-ethyl-1-naphthol, 2-(2-hydroxyethyl)-1-naphthol;
2-propyl-1-naphthol, 2-(3-hydroxypropyl)-1-naphthol.

4-aminophenols are useful in the present invention to conform to the general formula II.

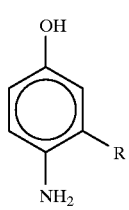

(II)

wherein R is $C_1$–$C_6$ alkyl or $C_1$–$C_6$ monohydroxyalkyl.

Preferred 4-aminophenols include:

3-methyl-4-aminophenol, 3-hydroxymethyl-4-aminophenol 3-ethyl-4-aminophenol, 3-(2-hydroxyethyl)-4-aminophenol 3-propyl-4-aminophenol, 3-(3-hydroxypropyl)-4-aminophenol.

The 2-substituted naphthol of formula I and the p-aminophenol of formula II are present in the compositions in amounts such that when reacted in the presence of an oxidizing agent a tinctorially effective amount of an oxidation hair dye is produced.

The hair dye preparations of the present invention may be formulated into cosmetic preparations such as solutions, creams, lotions, gels or emulsions. Also, in accordance with the invention, the compositions may in addition to the mixture of the coloring components (i.e., dye intermediate of formula II and coupling agent of formula I) include other coloring components (e.g. couplers and/or intermediates), as well as components commonly associated with the formulation of solutions, creams, lotions, gels or emulsions, and the like. For example, components such as wetting agents or emulsifying agents from the categories of anionic or non-ionic surfactants, such as sulfates of fatty alcohols, alkanolamides of fatty alcohols, alkyl sulfonates, alkylbenzene sulfonates, oxyethylated fatty alcohols, oxyethylated nonylphenols. Additionally, thickeners, such a fatty alcohols, starch, cellulose derivatives, paraffin oil and fatty acids, as well as hair-care substances, such as lanolin derivatives, cholesterol and pantothenic acid, may be formulated into the compositions of the invention.

When formulated as a lotion, the compositions of the invention may contain organic solvents to assist in dissolving the dye precursors. Accordingly, the organic solvent content of the lotion may be from 0% to about 20%, preferably about 1% to 15%. Typically useful solvents include alcohols containing up to three carbon atoms, such as ethanol and isopropanol, polyhydroxy alcohols, such as propylene or hexylene glycol, and lower alkyl ethers thereof, such as ethoxy ethers.

It should be noted that unless otherwise indicated to the contrary all percents specified herein are percent by weight and are based upon the total weight of the composition.

In addition, the hair dyeing compositions in accordance with the present invention may optionally contain conventionally-used adjuvants and cosmetic additives, or mixtures thereof, to achieve the final formulations. Examples of such additives include, but are not limited to, anti-oxidants, e.g. ascorbic acid, erythorbic acid, or sodium sulfite, to inhibit premature oxidizing; oxidizing agents, fragrances and/or perfume oils; chelating agents; emulsifiers; coloring agents; thickeners; organic solvents; opacifying agents; dispersing agents; sequestering agents; hair-care substances; humectants; anti-microbials; acidifying agents and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, *Cosmetics: Science and Technology*, Vol. 2, Second Edition, (1972).

Thickeners that may be used in the compositions of the present invention include a variety of fatty acid soaps and associative polymeric thickeners. The fatty acid soaps are alkali metal salts or alkanolamine salts of fatty acids with $C_{10}$–$C_{16}$ alkyl side chains. The preferred fatty acids include oleic acid, myristic acid, stearic acid and lauric acid, which are generally present in the compositions of the invention at about 0.5% to 20%, preferably about 1% to 10%. Associative thickeners are polymers that can thicken solutions at low concentrations. Among the associative thickeners that are useful in the compositions of the present invention are acrylates copolymer (sold by Rohm and Haas under the trade name Aculyn-33), ceteareth-20 acrylates/steareth-20 methacrylate copolymer (sold by Rohm and Haas under the trade name Aculyn-22), acrylates/steareth-20 itaconate copolymer and acrylates/ceteth-20 itaconate copolymer. Another class of associative thickeners useful in the compositions of the present invention include the copolymers of polyurethane and polyethylene glycol or polyetherurethanes. One such illustrative material is sold by Rohm and Haas under the trade name Aculyn-44. The associative polymeric thickeners are generally present in the compositions of the invention at about 0.1% to 10%, preferably about 0.5% to 5%.

The oxidative coupling, i.e., the development of the dye, can, in principle, be performed with atmospheric oxygen to produce the final color product on the hair. However, chemical oxidizing agents are suitably and preferably used. A preferred oxidizing agent for use as a developer or developing agent with the primary intermediates and the couplers of the invention is hydrogen peroxide, although other peroxides may be employed. These include, for example, urea peroxide, melamine peroxide, perborates and percarbonates such as sodium perborate or percarbonate. The concentration of peroxide in the developer may be from about 0.5% to about 40%, preferably about 0.5% to 30%. If the preferred hydrogen peroxide is employed, the concentration will be from about 0.5% to about 12%, preferably about 3% to 9%.

The compositions of the invention may include a typical anionic, cationic, nonionic or amphoteric surfactant.

The anionic surfactants include the variety of alkyl sulfates, alkylether sulfates, alkyl sulfonates, alkyl sulfosuccinates and N-acyl sarcosinates. The commonly-used anionic surfactants are sodium and ammonium lauryl sulfates, sodium and ammonium laureth sulfate and alpha olefin sulfonates. Anionic surfactants are generally present in the compositions of the present invention at about 0.1% to 15%, preferably about 0.5% to 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauramide DEA; lauramide MEA; isopropyl palmitate, isopropyl stearate and decylpolyglucoside. Nonionic surfactants are generally present in the compositions of the present invention at about 0.1% to 15%, preferably about 0.5% to 10%.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to 10%, preferably 0.5% to 5%, of the final composition.

Amphoteric surfactants may be employed in the compositions of the present invention. Amphoteric surfactants are surface active chemicals that possess a positive and a negative charge in the same molecule and behave as a cation, an anion, or both, depending upon the pH of the medium and the nature of the amphoteric molecule. In general, the positive charge is located on a nitrogen, while the negative charge is carried by a carboxyl or sulfonate group. There are a large number of amphoteric surfactants that are suitable for use in the present invention, including, for example, the well-known betaines, sultaines, glycinates and propionates that may generally be represented by the following structural formulae:

1. BETAINES:

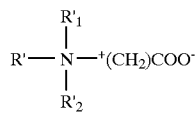

2. SULTAINES:

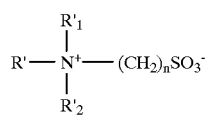

3. PROPIONATES:

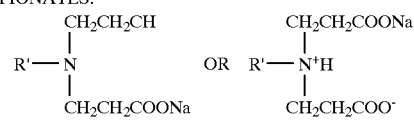

4. GLYCINATES:

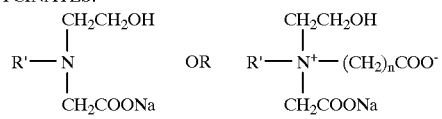

In these formulae, R' is an alkyl or alkylamide group containing from 10 to 20 carbon atoms. $R'_1$ and $R'_2$ are alkyl or hydroxyalkyl groups, which may be the same or different, and contain up to five carbon atoms. n is a positive integer from one to five.

The selection of the amphoteric surfactant or mixture of surfactants for use in the present compositions and methods is not critical. The surfactant may be selected from among those suggested above, or from any of a number of other known amphoteric surfactants. The amount of amphoteric surfactant in the compositions of the present invention is normally from about 0.5% to about 15%, preferably about 2% to 10%.

Depending on the final formulated preparation, the compositions in accordance with invention may be weakly acidic, neutral or alkaline. In particular the pH of the prepared compositions can range from about 5 to 11. Preferred is a pH range of about 8 to 10. Any of a wide variety of alkaline reagents can be used to adjust the pH of the hair coloring compositions. Such alkaline reagents include ammonium hydroxide, sodium hydroxide, potassium or calcium hydroxide, sodium or potassium carbonate, sodium or potassium borate, sodium phosphate, sodium silicate, guanidine hydroxide, or any one of the alkylamines or alkanolamines, for example, ethylamine, triethylamine, tris (hydroxymethyl)methylamine, ethanolamine, diethanolamine, triethanolamine, aminomethylpropanol, aminomethylpropanediol and the like. The preferred alkaline reagents are ammonium hydroxide, sodium carbonate, ethanolamine and aminomethylpropanol. With the reagents listed above, the selected pH will generally be achieved if the composition contains from about 0.1% to 15%, preferably about 0.5% to 5% of an alkaline reagent.

The application of the dyeing components is carried out by methods familiar to those in the art, for example, by mixing the hair dyeing preparation with an oxidant shortly before use, or at the time of applying the mixture onto the hair. On the hair, the compositions form a stable formulation preferably, with enough consistency and body to remain on the hair during the complete coloring period without dripping or running. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 10 to 45 minutes, preferably approximately 30 minutes), the hair is then rinsed then, optionally, shampooed. The application temperature is in the range of about 15° C. to 50° C.

Those in the art will appreciate that the compositions and methods of the present invention are appropriate for the dyeing of keratinous fibers, including the hair fibers of animals and humans, with particular application to the oxidative coloring of human hair.

As mentioned above, the hair dyeing compounds in accordance with the invention produce when coupled a particularly intense color. Dye precursors I and II may be used in conjunction with other primary intermediates and couplers as well as other components, as needed or desired. The colors obtained provide strong fastness to light, shampooing or washing, rubbing or abrasion.

The compositions of this invention may be separately provided in a kit or packaged form ready for mixing by the user, either professional or personal, to initiate the dyeing process. The kit provided in accordance with this invention comprises containers for housing the developer and the dye precursors, such as the primary intermediate(s) and coupler (s). In the most convenient form, there will be two containers, one containing the dye intermediates, e.g., as a lotion; the other containing the oxidizing agent.

The method of the invention comprises applying a mixture of the dye precursors, and other additives if necessary or desired, to the hair to be colored and allowing the resultant composition mixture to remain in contact with the hair until the desired hair color has been attained, after which time the composition is removed from the hair as is conventionally known.

The invention is further described by way of the examples below.

The following comparative compositions A and B were prepared (Table 1)

TABLE 1

Compositions A and B

| | A (%) | B (%) |
|---|---|---|
| Water | 44.50 | 44.50 |
| Lactic acid | 10.00 | 10.00 |
| Monoethanolamine | 12.00 | 12.00 |
| Oleic acid | 0.50 | 0.50 |
| Cocamidopropyl betaine | 17.00 | 17.00 |
| Sodium sulfite | 0.10 | 0.10 |
| EDTA | 0.10 | 0.10 |
| Erythorbic acid | 0.40 | 0.40 |
| 3-methyl-4-aminophenol | 1.00 | |
| 4-Aminophenol | | 0.87 |
| 2-Methyl-1-naphthol | 1.28 | 1.28 |
| Water | QS 100 | QS 100 |
| Color | Red | Orange-Red |

The color uptake (shown in Table 2) was evaluated by the use of the same molar concentration of 4-aminophenol and 2-methyl-1-naphthol. The procedure used is as follows:

100 g of the composition are mixed with 100 g of hydrogen peroxide (20 Volume). The resulting mixture is applied to bleached and gray hair and permitted to remain in contact with the hair for 30 minutes. The thus dyed hair is then shampooed and rinsed with water and dried. Tristimulus values are then determined using a Hunter Tristimulus Colorimeter. L is a measure of lightness and darkness (in other words, the depth of color on the hair tress). The Tristimulus a value is an indicator of the degree of green and red. The Tristimulus b value is an indicator of the degree of yellow and blue.

TABLE 2

Tristimulus Values of 4-aminophenol derivatives and 2-methyl-1-naphthol

| | gray tress | | | bleached tress | | |
|---|---|---|---|---|---|---|
| | L | a | b | L | a | b |
| 4-Aminophenol | 16.74 | 10.08 | 4.65 | 19.47 | 23.44 | 8.40 |
| 3-methylPAP | 16.33 | 11.42 | 2.51 | 15.82 | 19.08 | 4.53 |

1. Wash fastness test

The dyed bleached tresses were immersed in 100 g of 10% Herbal Essences® shampoo from Clairol® and shaken for 3 hours. After rinsing with water, the tress was dried and examined by Hunter Colorimeter. Tristimulus values and overall color changes are reported in Table 3, which follows.

TABLE 3

Tristimulus values of 3 hour wash fastness study

HUNTER VALUES

| | | Before Washing | | | 3 Hour Wash Fastness | | | |
|---|---|---|---|---|---|---|---|---|
| Dye | Hair | L | a | b | L | a | b | ΔE |
| PAP + 2MN | bleached | 19.47 | 23.44 | 8.4 | 32.15 | 20.86 | 11.81 | 13.38 |
| 3-MePAP + 2MN | bleached | 15.82 | 19.08 | 4.53 | 23.26 | 21.92 | 5.74 | 8.06 |

PAP = 4-aminophenol, 2MN = 2-methyl-1-naphthol
3-MePAP = 3-methyl-4-aminophenol

We claim:

1. In an oxidative dye composition for dyeing a keratin fiber, the composition containing a primary intermediate, a coupler, and a cosmetically acceptable vehicle, the primary intermediate and the coupler being present in respective amounts such that in the presence of an oxidizing agent will they react to produce a tinctorially effective amount of an oxidation dye, the improvement comprising the coupler is a 2-substituted-1-naphthol having the formula I

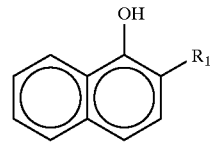

(I)

wherein $R_1$ is $C_1-C_6$ alkyl or a monohydroxy $C_1-C_6$-alkyl, and the primary intermediate is a compound of the formula II:

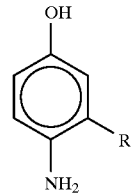

(II)

wherein R is a $C_1-C_6$ alkyl or a monohydroxy $C_1-C_6$-alkyl.

2. The composition according to claim 1, wherein the compound of formula I is selected from the group consisting of 2-methyl-1-naphthol, 2-ethyl-1-naphthol, 2-propyl-1-naphthol, 2-hydroxymethyl-1-naphthol, 2-(2-hydroxyethyl)-1-naphthol and 2-(3-hydroxypropyl)-1-naphthol.

3. The composition of claim 1, wherein the primary intermediate is 3-methyl-4-aminophenol, 3-ethyl-4-aminophenol, or 3-propyl-4-aminophenol, 3-hydroxymethyl-4-aminophenol, 3-(2-hydroxyethyl)-4-aminophenol or 3-(3-hydroxypropyl)-4-aminophenol.

4. The composition according to claim 1, wherein the primary intermediate is 3-methyl-4-aminophenol and the coupler is 2-methyl-1-naphthol.

5. In a method for dyeing hair including the steps of reacting a primary intermediate with a coupler in the presence of an oxidizing agent to produce a tinctorially effective amount of oxidation hair dye and contacting a hair fiber with such dye, the improvement comprising the coupler is a 2-substituted-1-naphthol compound having the formula I:

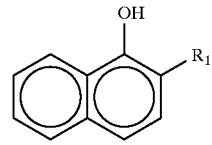

(I)

wherein $R_1$ is $C_1-C_6$ alkyl or a monohydroxy $C_1-C_6$-alkyl, and the primary intermediate is a compound of the formula II:

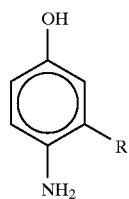

(II)

wherein R is $C_1$–$C_6$ alkyl or a monohydroxy $C_1$–$C_6$-alkyl.

6. The method according to claim 5, wherein the compound of formula I is selected from the group consisting of 2-methyl-1-naphthol, 2-ethyl-1-naphthol, 2-propyl-1-naphthol, 2-hydroxymethyl-1-naphthol, 2-(2-hydroxyethyl)-1-naphthol and 2-(3-hydroxypropyl)-1-naphthol.

7. The method according to claim 5, wherein the primary intermediate is 3-methyl-4-aminophenol.

8. The method according to claim 5, wherein the primary intermediate is 3-methyl-4-aminophenol and the coupler is 2-methyl-1-naphthol.

9. The composition according to claim 1, further comprising at least one material selected from the group consisting of perfumes, antioxidants, sequestering agents, alkalizing agents, acidifying agents and developers.

10. The composition according to claim 1, further containing at least one other primary intermediate or coupler other than I or II.

11. The method according to claim 5, wherein the step of reacting the coupler of formula I with the primary intermediate of formula II is carried out in the presence of at least one other primary intermediate or coupler other than the coupler of formula I or the primary intermediate of formula II.

* * * * *